(12) United States Patent
Malanowska-Stega et al.

(10) Patent No.: US 8,348,856 B1
(45) Date of Patent: Jan. 8, 2013

(54) SIMULTANEOUS MULTIPLE METHOD OUT-PATIENT UTERUS BIOPSY DEVICE AND METHOD

(76) Inventors: Zanetta Malanowska-Stega, Bronx, NY (US); Giuseppe DelPriore, Irvington, NY (US)

( * ) Notice: Subject to any disclaimer, the term of this patent is extended or adjusted under 35 U.S.C. 154(b) by 321 days.

(21) Appl. No.: 12/639,600

(22) Filed: Dec. 16, 2009

Related U.S. Application Data

(60) Provisional application No. 61/138,055, filed on Dec. 16, 2008.

(51) Int. Cl.
*A61B 5/00* (2006.01)
(52) U.S. Cl. ........................ 600/565; 600/571
(58) Field of Classification Search .................. 600/569, 600/562–567, 571
See application file for complete search history.

(56) References Cited

U.S. PATENT DOCUMENTS

| | | | | |
|---|---|---|---|---|
| 4,662,381 A | * | 5/1987 | Inaba | 600/569 |
| 6,036,658 A | * | 3/2000 | Leet et al. | 600/569 |
| 2002/0161313 A1 | * | 10/2002 | Sak | 600/569 |
| 2004/0116827 A1 | * | 6/2004 | Tiberio | 600/569 |
| 2008/0188769 A1 | * | 8/2008 | Lu | 600/569 |

* cited by examiner

*Primary Examiner* — Max Hindenburg
(74) *Attorney, Agent, or Firm* — Steven M. Hoffberg; Ostrolenk Faber LLP

(57) ABSTRACT

A biopsy device, comprising a flexible coaxial structure, comprising an obturator within a sheath, the obturator being adapted to be displaced with respect to the sheath along the coaxial axis by a force applied at a proximal end; a disruptor, at a distal end of the obturator, adapted to disrupt a tissue surface to free cells therefrom, having a first position covered within the sheath and a second position freely extending beyond the sheath; an element, having a fixed position on the obturator, and a close clearance with respect town inner surface of the sheath, such that a retraction of the obturator within the sheath causes an associated change in pressure in a space between the obturator distal to the element and the sheath, to thereby draw fluid proximate to an end of the sheath within the sheath.

16 Claims, 5 Drawing Sheets

SIMULTANEOUS MULTIPLE METHOD OUT-PATIENT UTERUS BIOPSY DEVICE AND METHOD

FIELD OF THE INVENTION

The present invention provides a system and method for performing a biopsy of the uterus. More particularly, it is a mechanical device that performs a mechanical disruption of the uterus, especially the endometrium, and simultaneously aspirates the residue of the disruption.

BACKGROUND OF THE INVENTION

Current biopsy devices and methods do not consistently provide an adequate sample to diagnose uterine abnormalities. For instance, if a cancer exists on the inside of the uterus, i.e. the endometrium, current devices and methods may miss the cancer and preclude an accurate diagnosis. To ensure an adequate and accurate specimen currently often requires a painful and dangerous series of procedures.

For example, the Cook Medical Tao Brush™ I.U.M.C. Endometrial Sampler, and the Pipelle endometrial biopsy device (See, Sierecki A R, Gudipudi D K, Montemarano N, Del Priore G., "Comparison of endometrial aspiration biopsy techniques: specimen adequacy." *J Reprod Med.* 53(10):760-4, 2008 October); J. A. Maksem: "Ciliated Cell Adenocarcinoma of the Endometrium Diagnosed by Endometrial Brush Cytology and Confirmed by Hysterectomy: A Case Report Detailing a Highly Efficient Cytology Collection and Processing Technique," Diagnostic Cytopathology, 16 (1997), 78-82, expressly incorporated herein by reference. See, U.S. Pat. Nos. 6,336,905, 7,207,951, 7,004,913, 6,676,609; 6,336,905; 5,456,265, 5,792,074, 5,146,928, 5,129,402, 4,157,709, 6,258,044, 5,462,063, 4,951,684, 4,054,127, 5,713,369, 6,193,674, 3,881,464, 4,127,113, 4,227,537, 4,759,376, 4,762,133, 4,873,992, 5,738,109, 5,201,323, 4,235,244, 4,754,764, 4,763,670, 4,966,162, 5,133,361, 5,184,626, 5,217,023, 6,193,674, 6,346,086, 6,387,058, 4,245,653, 6,059,735, 6,191,365, 6,278,057, each of which is expressly incorporated herein by reference.

The currently available options fall into two categories. The first are devices and methods that can be used in the office. These are usually thin devices 2-5 mm diameter that rely on either a weak suction or a disruption of the uterus. These are relative safe options but are not considered sufficiently accurate. The other category consists of larger devices that require more analgesics and even an operating room. This category includes the traditional dilation and curettage, i.e. D&C, and hysteroscopy. This category is more dangerous and painful than the first category. Neither category consistently gives an adequate, accurate and safely obtained sample and diagnosis in every case.

Endometrial sampling has become an integral part of the workup of pre-menopausal and postmenopausal women who are having abnormal uterine bleeding. Approximately over one million endometrial sampling procedures are done in the United States annually. Of the women born today, 2.45% (1 in 41) will be diagnosed with cancer of the uterus sometime during their lifetime. Therefore, theoretically 1 in 41 women will need an endometrial biopsy sometime in their lifetime.

Despite the large number of endometrial biopsies performed, limited information is available on the best technique to use with an aspiration type endometrial biopsy device (e.g. Pipelle, Cooper Surgical, Inc. Trumbull, Calif.). A slight difference in sensitivity and specificity of any screening procedure will have a great impact on the general population in identifying cancer especially for a test performed so frequently.

Specimen adequacy is the important factor for a procedure to be accurate in detecting abnormal pathology, especially a potential malignancy, precancerous or early cancer lesion. Different endometrial biopsy techniques are used with the aspiration device; e.g. "cork-screw", "D&C", or a combination of both with little objective data on what technique is best.

Most tests have an inherent sensitivity and specificity. However alteration in technique can be an important part of the test performance. We noticed that some members of our faculty group practice had different techniques based on intuition, e.g. povidone-iodine cleansing before endometrial biopsy. A literature reviewed and survey of the participating clinicians could not come up with a published evaluation of the different aspiration biopsy techniques used. We felt that the potential influence of these different techniques on the test characteristics of a test done more than one million times each year was important enough to begin an investigation of this area using a convenient sample and a retrospective chart review.

Based upon our analysis, the combined technique is significantly better than using either technique alone. Due to the large number of endometrial biopsies performed each year, even a small difference in test characteristics can have significant clinical ramifications.

Endometrial biopsy in the office setting, which consists of endometrial sampling using an aspiration biopsy device, has been shown to have sensitivity equivalent to that of dilatation & curettage (D&C). Its advantages include lower cost, it does not require anesthesia and it can be carried out in an office setting. Analyses have shown that a D&C is more costly and no more accurate in diagnosing endometrial abnormalities than the aspiration biopsy device. Aspiration biopsy device has been shown in repeated controlled clinical trials to be as effective as a D&C in diagnosing malignancy.

Although the aspiration biopsy device can detect cancer accurately, they may not able to detect tumors localized to a polyp or a small area of endometrium. Because of this variable and others, the sensitivity of an aspiration biopsy device in detecting uterine cancer varies in studies from 67% to 100% with an overall specificity of 100%. Huang et al. study found that an aspiration biopsy device had a sensitivity of 99.2% in pinpointing high-grade cancer and a sensitivity of 93% in detecting low-grade malignancies; the sensitivities as defined for D&C were 100% and 97% respectively. Low cost and accuracy dictate that an office, aspiration biopsy device should be used as the frontline test for endometrial sampling and the detection of endometrial cancer.

The National Cancer Institute (NCI, 2008) has stated that there is insufficient evidence to establish whether a decrease in mortality from endometrial cancer occurs with screening by endometrial sampling. The NCI notes that based on solid evidence, endometrial biopsy (sampling) may result in discomfort, bleeding, infection, and in rare cases uterine perforation. In addition, risks associated with false-positive test results include anxiety and additional diagnostic testing and surgery. Furthermore, endometrial cancers may be missed on endometrial sampling.

Endometrial sampling by means of biopsy for histological examination in the diagnostic evaluation of abnormal uterine bleeding in women suspected of having endometrial hyperplasia or endometrial carcinoma is a minimally invasive alternative for dilatation and curettage (D&C) or hysteroscopy. The Pipelle endometrial sampling device is the most popular method for sampling the endometrial lining (Guido, 2008). Various types of brushes have also been used for endometrial sampling. Although the brush appears to be as effective or better than other blind methods of endometrial sampling, these devices have been evaluated in only a few studies with small numbers of subjects (Critchley, et al., 2004; Yang, et al., 2002; Del Priore et al., 2001; Yang & Wan, 2000; Maksem, et al., 2000). In one of the larger comparative trials, 101 women (aged 35 to 86 years) with clinical indications for endometrial biopsy underwent a brush biopsy (Tao Brush, Cook OB-GYN, Bloomington, Ind.) and a Pipelle biopsy (Cooper Surgical, Shelton, Conn.) during one office visit. Twenty-two had cancer or atypia, the others had benign diagnoses. When correlated with the final diagnosis, sensitivity for the Tao Brush and Pipelle were 95.5% and 86%, respectively, and specificity was 100% for both (Del Priore, et al., 2001).

According to the company's website (Gynecor™, Glen Allen, Va.), the TruTest™ for total uterine testing is the first test that is able to detect endometrial and cervical cancer, HPV, chlamydia and gonorrhea from the same specimen. Using the Tao Brush, a sampling of the uterine lining is taken and the brush is sent to Gynecor™ for both histology and cytology examination. The testing kit provided by Gynecor has one Tao Brush (used for the collection of endometrial tissue) and two cytobrushes (one is used to clean mucus and debris from the cervix and the second is used for enhanced cell and tissue collection from the squamo-columnar junction of the uterine cervix). The Tao Brush is an FDA, Class II device.

The use of histology for endometrial examination depends on having enough tissue to yield an accurate test result. However, a tissue specimen is sometimes hard to collect, especially in post-menopausal women. Gynecor fixative can be used for both histology and cytology. According to Gynecore's website, "Cytologies are very important because they add about 20% more information than is obtained with just the histology. Using this method, Gynecor has been able to diagnose ovarian carcinoma in transit, endometrial intraepithelial neoplasia and endometrial intraepithelial carcinoma."

In a feasibility study, Maksem, et al. (1997) compared the cytologic diagnosis to the histologic diagnosis of endometrium collected from 100 hysterectomy specimens using the Tao Brush and the CytoRich fixative system. Interpretative algorithms that translate histopathologic to cytopathologic diagnoses were used. The authors reported that cytology separated benign endometrium, low-grade (non-atypical) hyperplasia, high-grade (atypical) hyperplasia/FIGO Grade I adenocarcinoma, and higher-grade carcinomas from one another. Endometrial atrophy was diagnosed in 3 patients whose histology showed clinically asymptomatic, benign fibrous endometrial polyps. A low volume of abnormal cell aggregates interpreted as endometrial intraepithelial carcinoma was detected in 1 patient whose initial histology was reported as simple hyperplasia, but whose histology on review after p53 staining revealed intraepithelial surface cancer. In the remaining 96 cases, the cytologic diagnosis consistently represented the histologic diagnosis of the hysterectomy specimen. On a case-by-case basis, any one cytology slide accurately represented the diagnosis of the other cytology slides. The authors concluded that endometrial brushing with suspension fixation is (i) uniform, (ii) three-dimensional structures among cell aggregates are preserved, which allows pattern-based histologic diagnostic criteria to be applied to cytologic samples, and (iii) only a limited number of slides need to be examined.

Van den Bosch, et al. (1998) evaluated the value of cervical cytology in menopausal women at high risk for endometrial disease in 128 consecutive menopausal women presenting with uterine bleeding (n=116) or in whom endometrial cells were found on a previous cervical cytology smear (n=12). An endo- and ecto-cervical smear was taken before hysteroscopy with curettage and the results of the cervical cytology were compared with the endometrial histology. Endometrial carcinoma was diagnosed by endometrial sampling in 6 women. In 2 of these cases cervical smears did not contain endometrial cells. The presence of endometrial cells on ecto-cervical cytology showed a sensitivity of 67% and a specificity of 78% for endometrial carcinoma versus 80% and 76%, respectively, for endo-cervical cytology. The positive predictive value for endometrial malignancy of the presence of endometrial cells on cervical cytology ranged between 13% and 17%. The presence of atypical endometrial cells on cervical smear was associated with endometrial malignancy in almost half the cases. The authors concluded that cervical cytology is of limited value in the diagnosis and the management of post-menopausal endometrial disease.

Dijkhuizen, et al. (2000) performed a meta-analysis to assess the accuracy of endometrial sampling devices in the detection of endometrial carcinoma and atypical hyperplasia. The authors searched the literature for studies published between 1966 and 1999 that compared the results of endometrial sampling with findings at D&C, hysteroscopy, and/or hysterectomy. They found 39 studies that included 7,914 women. For each study, the number of patients in which endometrial sampling failed as well as the sensitivity and specificity for the detection of endometrial carcinoma and atypical hyperplasia was calculated. The detection rate for endometrial carcinoma was higher in post-menopausal women compared with pre-menopausal women. In both post-menopausal and pre-menopausal women, the Pipelle was the best device, with detection rates of 99.6% and 91%, respectively. For the detection of atypical hyperplasia, there was only one study that reported explicitly on post-menopausal women, thereby hampering the possibility of subgroup analysis. Again, the Pipelle was the most sensitive technique with a sensitivity of 81%. The specificity of all devices was greater than 98%. The authors concluded that endometrial biopsy with the Pipelle is superior to other endometrial techniques in the detection of endometrial carcinoma and atypical hyperplasia. The accuracy of the Pipelle is higher in post-menopausal women compared with pre-menopausal women.

Maksem (2000) reported performance characteristics of the ability of the Tao Brush in recognizing histological patterns in cytology preparations of endometrial brushings (n=113). Correlative tissue examinations comprising Pipelle (Prodimed, Neuilly-en-Thelle, France) biopsy, hysteroscopy and biopsy, D&C, and hysterectomy were available at for 59 cases. In 42 cases, cytology diagnoses could be compared to histology diagnoses. Twenty-five of 63 normal brushings were followed up; 14 were normal. Eleven Pipelle biopsies of cytologically atrophic endometrium were quantitatively limited and insufficient for diagnosis. Thirty-seven cases were abnormal, and 15 of these showed nuclear anaplasia. Twenty-eight of the abnormal cases were followed up. All correlative tissue examinations confirmed an abnormality. All 15 cases with nuclear anaplasia showed significant histopathology comprising atypical endometrial hyperplasia, endometrial intraepithelial neoplasia (RN), endometrial intraepithelial carcinoma (EIC), and invasive adenocarcinoma. There were 13 inadequate endometrial brushings. Three cases had insufficient cellular material. The remaining 10 cases were cellular but were mainly cervical/endo-cervical samples. Two of the cellular cases resulted from clinicians failing to replace the protective sheath over the brush bristles before removing the Tao Brush from the endometrial cavity. The remaining 11 cases resulted from inaccessibility of the uterine cavity due to a tight or stenotic cervix. The author concluded that (i) the Tao brush is a reliable uterine sampling device for outpatient assessment of the endometrium of women with patent cervices, (ii) endometrial cytology accurately represents atrophic endometrium, (iii) it is an effective case-finding tool for EIN and EIC, and (iv) women with tight or stenotic cervices are poor candidates for endometrial brushing, and may experience pain if the procedure is attempted.

In a case series on the use of the Tao Brush for endometrial biopsy, Wu, et al. (2003) reported that the sensitivity and specificity in identifying endometrial cancer was 100% and 96%; however, diagnosis relied mainly on histologic evaluation of hematoxylin and eosin-stained tissue sections and assessment of specimen adequacy was important when interpreting Tao Brush biopsies.

In an unblinded randomized trial, Critchley, et al. (2004) compared 3 outpatient methods of endometrial evaluation in terms of performance, patient acceptability and cost-effectiveness. Women referred for investigation and management of abnormal bleeding between January 1999 and May 2001 were evaluated using blind biopsy alone, hysteroscopy with biopsy, ultrasound evaluation including transvaginal ultrasound, and, in the low-risk group, the option of no investigation. Within this design, two devices for obtaining endometrial biopsy were compared, the Pipelle sampler and the Tao Brush. Minor adverse events (e.g., shock, patient distress) did not occur for ultrasound, but occurred in 16% and 10% of women for hysteroscopy and biopsy procedures respectively. Pipelle biopsy provided an acceptable endometrial sample for 79% of moderate-risk women, but only 43% of high-risk women. The Tao Brush gave similar performance in moderate-risk women (77%), but was more successful than the Pipelle sampler in post-menopausal (high-risk) women (72%).

To determine the performance characteristics of endometrial cytology for the detection of malignancy and atypical hyperplasia using liquid-based cytology specimens collected with the Tao Brush sampler, Kipp, et al. (2008) obtained brushings of the endometrial cavity from 139 hysterectomy specimens before routine histopathologic evaluation. Cytology specimens were fixed in PreservCyt and processed using ThinPrep technology. Cytology diagnoses were classified as non-diagnostic, negative, atypical, or positive for malignancy. Histopathologic findings were used as the gold standard for determining the performance characteristics of cytology. Histopathologic results from the 139 patients included 81 (58%) endometrial cancers, 7 (5%) complex hyperplasias with atypia, 2 (1%) complex hyperplasias without atypia, and 49 (35%) patients with benign histology. The number of specimens diagnosed cytologically as positive, atypical, negative, or non-diagnostic was 60 (43%), 40 (29%), 37 (27%), and 2 (1%), respectively. The overall sensitivity and specificity of cytology for detecting endometrial cancer and atypical hyperplasia were 95% and 66% when atypical cytology specimens were considered positive. The authors concluded that direct endometrial sampling by liquid-based endometrial cytology collected with the Tao Brush sampler produces specimens that contain cellular material that may be identified as endometrial cancer or atypical hyperplasia; however, both atypical and positive cytology diagnoses are indicators for triage to more specific methods of diagnosis.

Williams, et al. (2008) evaluated factors affecting the adequacy of pipelle and Tao Brush endometrial sampling. Women referred to an outpatient clinical for assessment of abnormal vaginal bleeding (n=200) were assigned to one of two risk groups: "high risk" for post-menopausal women and "moderate risk" for pre-menopausal women aged 40 years or older or with other risk factors. Women in each risk group had both Tao Brush and Pipelle biopsy and were then randomized to have either hysteroscopy and/or transvaginal ultrasound. Nulliparity was associated with failed insertion for both the Tao Brush and Pipelle (p<0.001). Among post-menopausal women, inadequate samples were associated with the Pipelle (p<0.001). Among pre-menopausal women with nulliparity, both the Tao Brush and Pipelle were associated with inadequate samples (p<0.001). A significantly greater proportion of women preferred the Tao Brush to the Pipelle.

Outpatient endometrial biopsy has a high overall accuracy in diagnosing endometrial cancer when an adequate specimen is obtained. A positive test result is more accurate for ruling in disease than a negative test result is for ruling it out. Therefore, in cases of abnormal uterine bleeding where symptoms persist despite negative biopsy, further evaluation will be warranted (Clark, et al., 2002). If the woman is post-menopausal and bleeding has not been persistent; a thin endometrial stripe in this setting is most consistent with atrophy and does not require further invasive studies. A thick endometrial stripe, persistent bleeding, or bleeding in a post- or peri-menopausal woman should be followed by additional endometrial sampling, such as hysteroscopy with curettage. In asymptomatic post-menopausal women, the decision to biopsy is also based upon a variety of factors, including cervical cytology showing endometrial cells or glandular abnormality, and risk factors for endometrial cancer, such as unopposed estrogen and tamoxifen use. In a completely asymptomatic post-menopausal woman with no risk factors and an endometrial stripe less than 5 mm, there is no need for biopsy. However, even one drop of blood in a post-menopausal woman not on hormone therapy constitutes a symptom and is an indication for biopsy.

Current evidence-based guidelines from leading medical professional organizations include no recommendation for endometrial or cervical cytology performed in conjunction with endometrial histology in the diagnostic evaluation of abnormal uterine bleeding in women suspected of having endometrial hyperplasia or endometrial carcinoma. There is insufficient evidence to support this approach.

The problems presented in existing tissue sampling devices are solved by the device and method of the present invention.

SUMMARY OF THE INVENTION

A preferred embodiment of the present invention provides a narrow cylindrical tube with a guidewire and biopsy sampling device at the end, similar to a Cook Medical (Bloomington, Ind.) Tao Brush™ I.U.M.C. Endometrial Sampler, modified such that surrounding the guidewire, proximal to the biopsy sampling device at the end of the guidewire, and disposed within the sheath, is a piston-like structure which, when the wire is withdrawn through the sheath, draws a vacuum and sucks fluid surrounding the guidewire into the sheath. A vacuum biopsy sampling device, such as the known Pipelle endometrial suction curette produces a vacuum and draws it into the sheath by a similar principle, but lacks the brush or other biopsy sampling device at its distal end.

The preferred device is a 1-3 mm diameter by 30-40 cm long coaxial "straw" that can easily pass into the uterus endometrial cavity with little or no discomfort. It is malleable but rigid enough to apply sufficient force to pass through the cervix. In the center of the outer sheath, which is an impermeable tube, a thinner inner insert can be extended beyond the end of the tube into the uterus. This inner obturator disrupts the uterus to loosen and collect a biopsy sample of the uterus.

The tissue sampling device includes a spirally twisted flexible wire with opposed proximal and distal ends. Also included is a plastic tube covering a significant portion of the wire to provide additional rigidity without making the overall brush stiff. Along the distal end portion of the wire is a brush that includes bristles that were used for collecting a tissue sample. The bristles are fixed within the spirally twisted wire near the distal end and are tapered from smaller to larger towards the distal end of the wire. Tapering of the bristles from the distal end of the device allows for more global tissue collection of the endometrium because of the shape of the endometrial cavity. An atraumatic bulb is located on the extreme distal end of the twisted wire.

Simultaneously withdrawal of the inner obturator back into the narrow cylindrical tube, the device creates a weak suction to collect the disrupted sample into the outer tube. The entire apparatus is then withdrawn from the uterus and the sample is collected by reversing the process outside the body.

In accordance with another embodiment, the plastic tube and twisted wire are contained within a sheath of shorter length than the twisted wire, such that the sheath can be moved along the plastic tube to the atraumatic bulb on the distal end of the twisted wire, thereby covering the brush during insertion and removal after tissue collection. Before insertion, the sheath can be moved into position over the distal end of the twisted wire to protect the brush during insertion. Having the brush covered during insertion also increases comfort for the patient and protects the brush from collecting tissue from unintended areas. The sheath is moved back toward the proximal end of the twisted wire after the device has been inserted to the proper collection depth, exposing the brush and allowing for collection of a tissue sample. The sheath may be moved to completely uncover the brush or may be moved in gradients to uncover portions of the brush. This allows the practitioner to adjust the effective collection area of the brush based on the anatomy of the patient. The plastic tube covering the wire is scored in centimeter gradations along the plastic tube with markings indicating the exact length of the brush inserted into the uterus, starting from the distal tip of the brush to the proximal end of the plastic tube. This allows the clinician to know how deeply the brush is inserted into the uterus. The sheath is approximately the same length as the plastic tube and in position to cover the brush bristles prior to insertion. The sheath may be formed of a clear material such that the gradations on the plastic tube may be viewed through the sheath. The ability to measure insertion depth increases the certainty that the tissue sample collected is from the correct area, After a tissue sample is collected from the proper area, while the tissue sampling device remains inserted, the sheath can be moved back along the distal end of the twisted wire to cover the brush bristles before removing the brush. This allows for the tissue sample to be protected on the brush within the sheath during removal.

Additionally, the gradations along the flexible tube allow the practitioner to measure the length of bristles exposed. As the practitioner pulls the sheath from its insertion position towards the handle, the further the sheath is pulled the more bristles are exposed. The gradations (ruler) provide a visual confirmation of this measurement and allow the practitioner to be precise in exposing only a certain length of the brush bristles. This measurement allows the practitioner to have better control of where the tissue is sampled and allows the practitioner to adjust the length of brush based on patient specific parameters; such as uterine size measured during previous tests inferred based on patient history. Control of brush exposure increases sampling precision and patient comfort.

By combining two or more methods into one device, the invention eliminates pain, discomfort, and inconvenience, e.g., a second procedure to obtain an adequate and accurate specimen. The multiple methods of specimen collection, e.g., disruption by physical means, and suction, used together, allows a gentler application of the individual methods, e.g. a gentle disruption and gentle suction applied simultaneously can replace a vigorous disruption, e.g. D&C, and a powerful suction. The combination of multiple gentler methods in one device is safer and more effective than any method alone. On the other hand, to the extent either of the multiple methods is acceptably used at the levels used when employed individually, the apparatus and method according to the present invention has the capacity to produce improved results. The simultaneous combination of multiple methods provides a consistently more satisfactory specimen and more accurate diagnosis.

The invention can be used in a doctor's office and does not need analgesics or an operating room. It is a safer, faster and less expensive improvement over current methods.

REFERENCES (INCORPORATED HEREIN BY REFERENCE)

Yang G C, Wan L S, Del Priore G. Factors influencing the detection of uterine cancer by suction curettage and endometrial brushing. J Reprod Med 2002; 47:1005-10.
Ries L A G, Melbert D, Krapcho M, Mariotto A, Miller B A, Feuer E J, Clegg L, Horner M J, Howlader N, Eisner M P, Reichman M, Edwards B K (eds). SEER Cancer Statistics Review, 1975-2004, National Cancer Institute. Bethesda, Md., seer.cancer.gov/csr/1975_2004/, based on November 2006 SEER data submission, posted to the SEER web site, 2007.
McCluggage W G. My approach to the interpretation of endometrial biopsies and curettings. J Clin Pathol. 2006; 59:801-12.
Dijkhuizen F P, Mol B W, Brolmann H A, Heintz A P. The accuracy of endometrial sampling in the diagnosis of the patients with endometrial carcinoma and hyperplasia: a meta-analysis. Cancer 2000; 89(8):1765-72.
Feldman S, Berkowitz R S, Tosteson A N. Cost-effectiveness of strategies to evaluate postmenopausal bleeding. Obstet Gynecol 1993; 81(6):968-75.
Grimes D A. Diagnostic dilation and curettage: A reappraisal. Am J Obstet Gynecol 1982; 142:1-6.
Ong S, Duffy T, Lenehan P, Murphy J. Endometrial pipelle biopsy compared o conventional dilatation and curettage. Ir J Med Sci 1997; 166:47-9.
Tahir M M, Bigrigg M A, Browning J J, Brookes S T, Smith P A. A randomized controlled trial comparing transvaginal ultrasound, outpatient hysteroscopy and endometrial biopsy with inpatient hysteroscopy and curettage. Br J Obstet Gynecol 1999; 106(12):1259-64.
Ferry J, Farnsworth A, Webster M, Wren B. The efficacy of the pipelle endometrial biopsy in detecting endometrial carcinoma. Aust N Z J Obstet Gynecol 1993; 33:1-76.
Guido R S, Kanbour-Shakir A, Rulin M, Christopherson Wash. Pipelle endometrial sampling: sensitivity in the detection of endometrial cancer. J Reprod Med 1995; 40:553-5.

Stovall T G, Photopulos G J, Poston W M, Ling F W, Sandles L G. Pipelle endometrial sampling in patients with known endometrial carcinoma. Obstet Gynecol 1991; 77:954-6.

Van den Bosch T, Vandendael A, Wranz P A, Lombard C J. Endopap-versus Pipelle-sampling in the diagnosis of postmenopausal endometrial disease. Eur J Obstet Gynecol Reprod Biol 1996; 64:91-4.

Huang G S, Gebb J S, Einstein M H, et al. Accuracy of preoperative endometrial sampling for the detection of high-grade endometrial tumors. Am J Obstet Gynecol 2007; 196:243.e1-243.e5.

Kozuka T: Patch testing to exclude allergic contact dermatitis caused by povidone-iodine. Dermatology 2002; 204 Suppl 1:96-8.

Borja J M, Galindo P A, Gomez E, Feo F. Contact dermatitis due to povidone-iodine: allergic or irritant?. J Investig Allergol Clin Immunol 2003; 13(2):131-2.

Naim N M, Mandy Z A, Ahmad S, Razi Z R M. The Vabra aspirator versus the pipelle device for outpatient endometrial sampling. Aust N Z J Obstet Gynecol 2007; 47(2):132-6.

Phillips V, McCluggage W G. Results of a questionnaire regarding criteria for adequacy of endometrial biopsies. J Clin Pathol. 2005; 58:417-9.

BRIEF DESCRIPTION OF THE DRAWINGS

FIG. 1 shows the inner obturator and disrupting elements, which may be, for example, a brush, tapered helical screw, loop or loop with brush elements, or the like;

DETAILED DESCRIPTION OF THE PREFERRED EMBODIMENTS

A preferred embodiment of the present invention consists of an outer thin walled tube (A) of variable diameter and length. In general dimensions are approximately 1.5 mm outside diameter and 1.4 mm inside diameter; length is between 20-50 cm. This tube may be a clear, malleable plastic tube, such as polyethylene. The inner obturator is preferably formed from a thin wire equivalent of approximately 0.1-0.2 mm diameter, having sufficient mechanical properties to convey the forces for extension and retraction during use. At one end, the one that enters the uterus, a disruptive enhancement is attached to the end. For example, the disruptive enhancement may have a screw like pattern mechanical attachment, a thin wire or multiple small semi-rigid projections that contact the uterus and loosen and collect the desired specimen. Alternatively, the disruptive enhancement may also include an enzymatic applicator and liquid based digestive enzymes that can be injected through the obturator tube (sheath), for example during extension of the obturator, or through a second lumen. A tight fitting ring around the obturator acts as a piston and creates the suction as the obturator is withdrawn through the outer tube.

Figure 1:
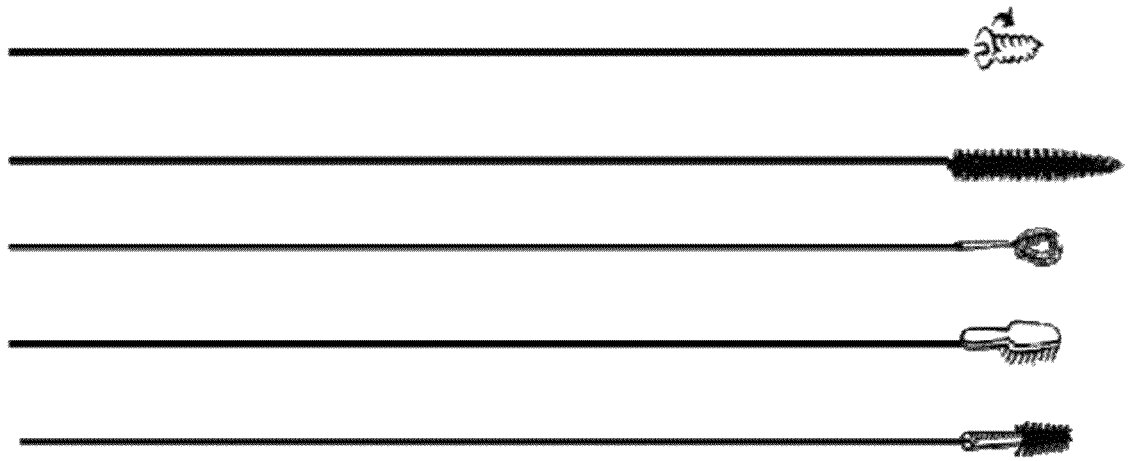

FIG. 1 shows the obturator, which is approximately 0.1-0.2 mm diameter with attached disrupting enhancements of various possible types, and is 45-50 cm long. The obturator is generally stiff, so that the pushing force is transmitted along it s length, within the tube, and thus can be extended and withdrawn. The clearance between the obturator and the inner diameter of the tube is such that a sample volume can be collected within the tube at the distal end, while supporting the obturator to effectively transmit the forces. The tube may have a taper, such that the diameter is greater near the distal end, where the ring moves and disruptive element is extended and retracted, than the proximal end. A plunger handle is provided at the proximal end for manual operation of the extension and retraction.

Figure 2:
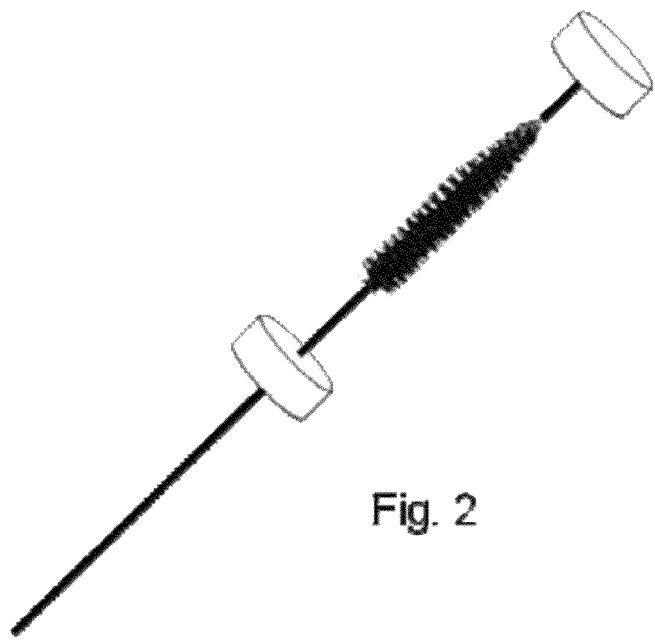
FIG. 2 shows a plunger elements affixed around the obturator.

FIG. 2 shows a tight clearance ring attached to obturator to create suction when withdrawn within the sheath.

Figure 3:
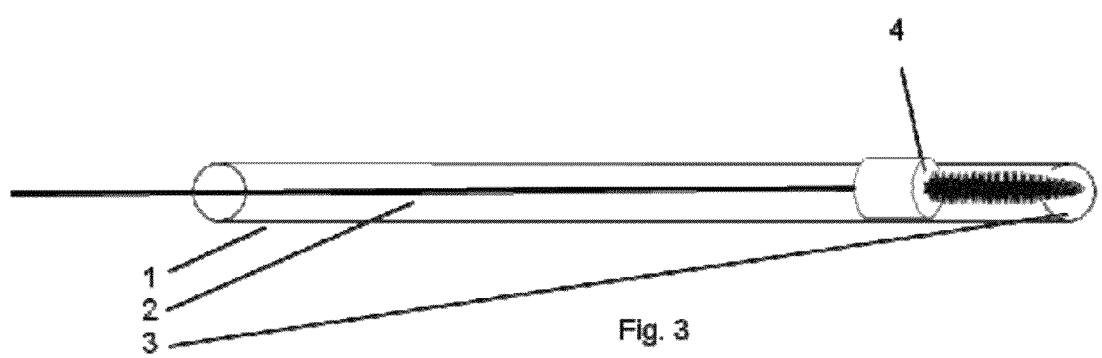
FIG. 3 shows the obturator within the sheath, with the disruptor retracted and the plunger, which is a ring tightly affixed to the obturator and having close clearance within the sheath.

FIG. 3 shows the obturator within the sheath, with the disruptor retracted and the plunger, which is a ring tightly affixed to the obturator and having close clearance within the sheath. In this case, the disruptor may be similar to that provided on the Tao Brush™, and, for example, may have a spherical knob at the end to prevent damage to tissue from the tip. Alternately, the disruptor may have bristles at the tip; in any case, a sharp thin tip is generally avoided to limit the risk of puncture.

Figure 4:
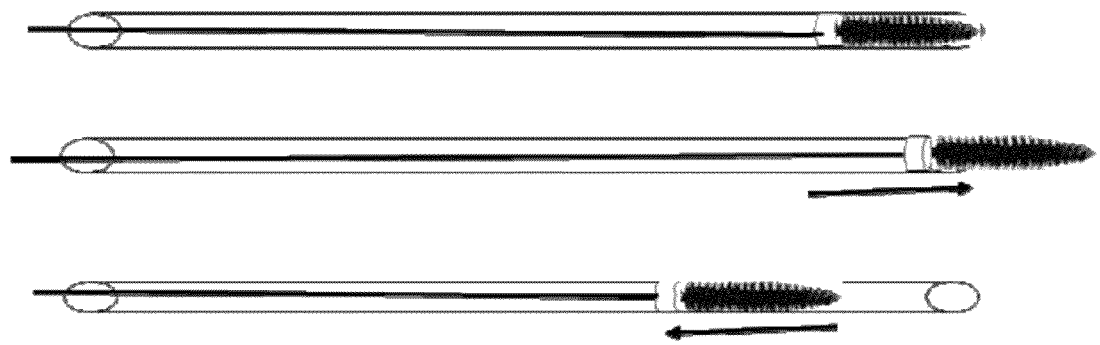
FIG. 4 shows three stages of operation of the biopsy device: initially retracted before use, extended to sample the tissue, and retracted with sample drawn into sheath.

FIG. 4 shows three stages of operation of the biopsy device. Initially, the obturator is retracted before use, with the disruptive enhancement within the sheath, so that tissue samples are not collected during insertion to the biopsy site. After positioning, the disruptive enhancement is extended from the sheath, to free cellular samples at the biopsy site. Finally, the disruptive enhancement is withdrawn back into the sheath, with the ring creating a suction within the sheath around the obturator to draw a volume of fluid into the sheath. The distal end of the biopsy device may have a greater inner diameter than the proximal end, permitting a larger disruptive enhancement than otherwise possible, and a larger volume of tissue sample to be drawn. The sheath, in that case, may have a constant outer diameter and a tapered wall thickness, a larger outer diameter, or both.

Figure 5:
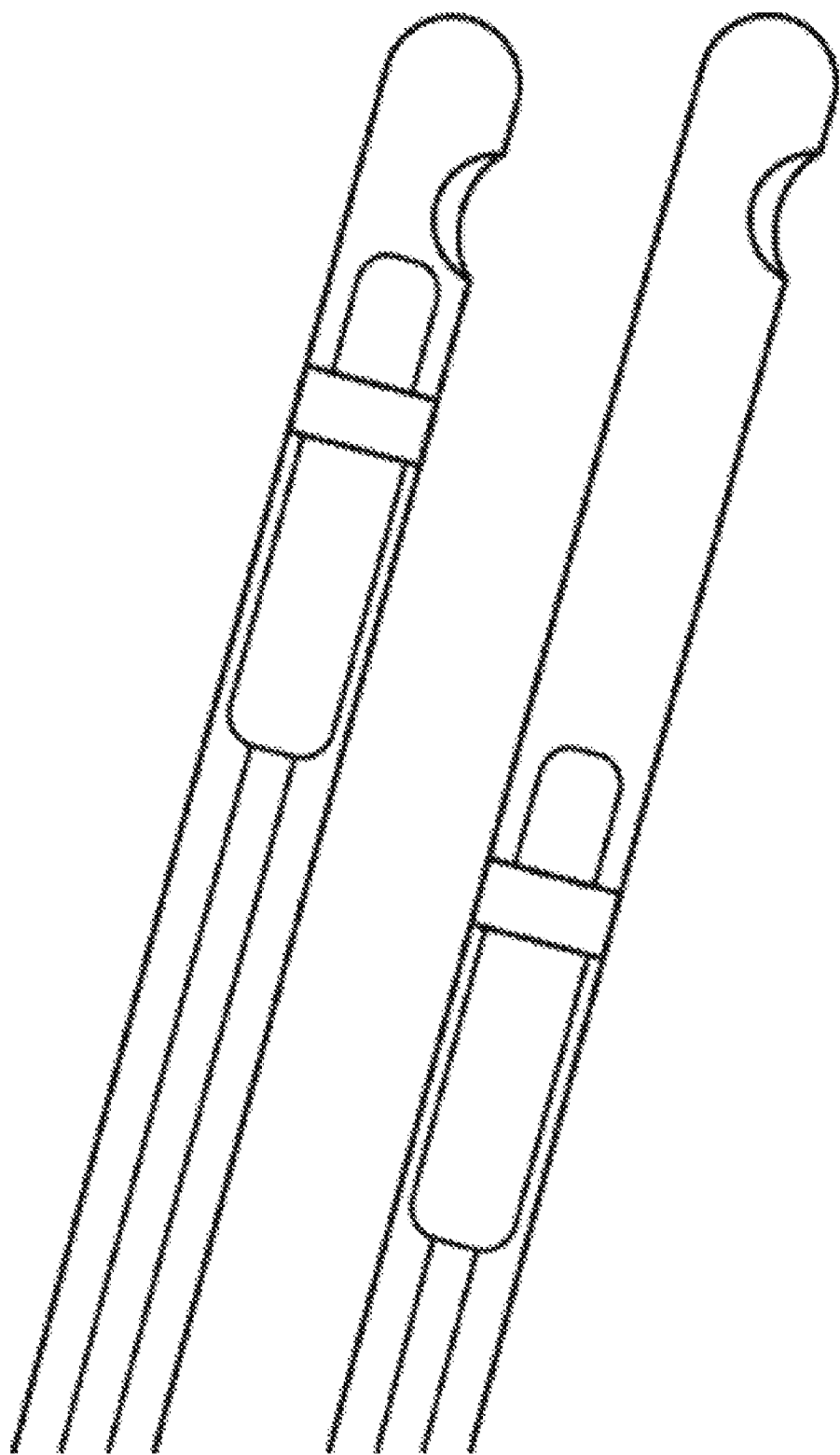
FIG. 5 shows a Pipelle endometrial biopsy device of the prior art, which lacks a disrupting device.

FIG. 5 shows a known Pipelle endometrial biopsy device, which lacks a disrupting device at its distal end. This device has an internal plunger, which creates a suction to draw a sample at the biopsy location.

Figure 6:
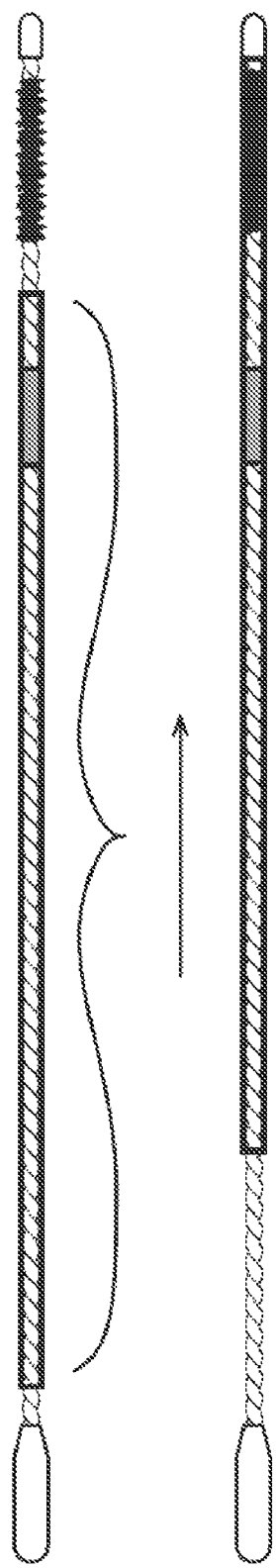
FIG. 6 shows views of a Tao Brush™ endometrial biopsy device of the prior art, which lacks an effective suction function.

FIG. 6 shows a known Tao Brush™ endometrial biopsy device, which lacks an effective suction function. Therefore, the amount of fluids surrounding the obturator collected is effectively limited, and the bulk of the sample collected is either attached to the brush at the distal end or is present in the fluids immediately proximal to the brush when it is retracted.

Figure 7:
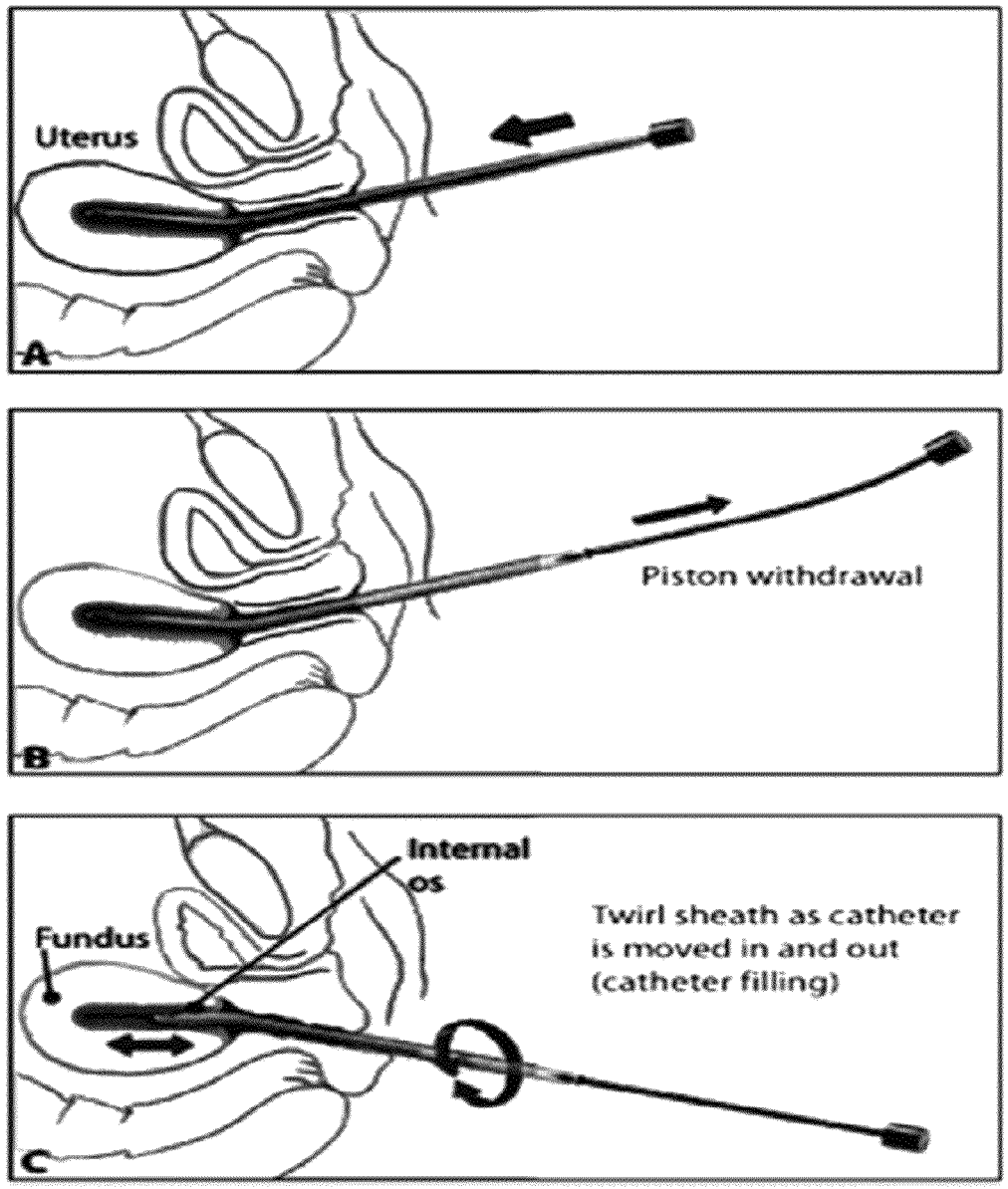
FIGS. 7A, 7B and 7C show representations of different stages of a biopsy.

FIG. 7 shows a representation of a biopsy procedure. The detail of the disruptive enhancement according to the present invention is not shown.

The invention may be used, for example, to sample the inside of the uterus to diagnose abnormalities. It can detect or exclude a cancer. It can obtain an adequate tissue sample to determine infertility causes.

What is claimed is:
1. An endometrial biopsy device, comprising:
 a flexible coaxial structure, comprising an obturator within a sheath, the obturator being configured to be displaced with respect to the sheath along the coaxial axis by a force applied at a proximal end, and the sheath having a cylindrical tip at a distal end configured to be inserted into an endometrial cavity;

a disruptor, at a distal end of the obturator, configured to disrupt an endometrial tissue surface to free cells therefrom, having a first position covered within the sheath and a second position freely extending beyond the distal end of the sheath; and an element, having a fixed position on the obturator proximally displaced from the disruptor, and having a dose clearance with respect to an inner surface of the sheath, such that a retraction of the element from the second position into the first position within the sheath causes an associated suction in a space between the obturator distal to the element and the sheath, to thereby draw and retain a fluid sample proximate to the distal end of the sheath within the sheath.

2. The endometrial biopsy device according to claim 1, wherein the disruptor comprises a brush having a plurality of bristles extending normal to the coaxial axis.

3. The endometrial biopsy device according to claim 1, wherein the obturator terminates in a blunt element.

4. The endometrial biopsy device according to claim 1, wherein the disruptor comprises a helical screw element.

5. The endometrial biopsy device according to claim 4, wherein the coaxial structure is configured to convey a torque from the proximal end to the distal end, thereby permitting a twisting of the disruptor during a biopsy procedure.

6. The endometrial biopsy device according to claim 1, wherein the obturator comprises a metal wire.

7. The endometrial biopsy device according to claim 1, wherein the sheath comprises a plastic tube.

8. The endometrial biopsy device according to claim 1, wherein the element comprises a ring formed around the obturator.

9. An endometrial biopsy method, comprising:

providing a flexible coaxial structure, comprising an obturator within a sheath, the obturator being configured to be displaced with respect to the sheath along the coaxial axis by a force applied at a proximal end, the sheath having a cylindrical tip at a distal end configured to be inserted into an endometrial cavity, and having a disruptor, at the distal end of the obturator, adapted to disrupt an endometrial tissue surface to free cells therefrom, having a first position covered within the sheath and a second position freely extending beyond the distal end of the sheath, and an element, proximally displaced from the disruptor, having a fixed position on the obturator, and a close clearance with respect to an inner surface of the sheath, such that a retraction of the element from the second position into the first position within the sheath causes an associated suction in a space between the obturator distal to the element and the sheath, to thereby draw and retain fluid proximate to the distal end of the sheath within the sheath;

inserting the flexible coaxial structure into the endometrial cavity with the disruptor in the first position;

extending the obturator from the sheath to the second position, and causing the disruptor to disrupt an endometrial tissue in the endometrial cavity;

retracting the obturator into the sheath into the first position, creating a suction around the obturator within the sheath, to draw fluid proximate to an end of the sheath within the sheath; and withdrawing the flexible coaxial structure from the endometrial cavity with the drawn fluid within the sheath.

10. The endometrial biopsy method according to claim 9, wherein the disruptor comprises a brush having a plurality of bristles extending normal to the coaxial axis, further comprising disrupting an endometrial lining with the brush.

11. The endometrial biopsy method according to claim 9, wherein the disruptor comprises a helical screw element, further comprising twisting the obturator to obtain an endometrial sample.

12. The endometrial biopsy method according to claim 11, further comprising twisting the obturator from the proximal end, wherein the obturator is configured to convey a torque from the proximal end to the distal end, thereby permitting a twisting of the disruptor during a biopsy procedure.

13. An endometrial biopsy device, comprising:

a narrow cylindrical tube configured to be inserted within a uterus;

a guidewire within the narrow cylindrical tube; and a biopsy sampling device at a distal end of the guidewire, having a piston-like structure surrounding the guidewire within the narrow cylindrical tube, proximal to the biopsy sampling device, wherein when the guidewire is withdrawn through the narrow cylindrical tube, said piston-like structure causes a suction that draws a vacuum and sucks fluid surrounding the guidewire into the sheath.

14. The endometrial biopsy device according to claim 13, wherein the narrow cylindrical tube is about 1-3 mm in diameter.

15. The endometrial biopsy device according to claim 13, wherein the narrow cylindrical tube is about 45 cm long and has a manually manipulable element for controlling the extension of the guidewire.

16. The endometrial biopsy device according to claim 13, wherein the guidewire comprises a spirally twisted flexible wire, wherein the biopsy sampling device comprises bristles at a distal end of the spirally twisted flexible wire having an atraumatic bulb located on the extreme distal end of the twisted flexible wire, and the narrow cylindrical tube has a diameter of about 1.4 mm.

* * * * *